(12) United States Patent
Matsuzaki

(10) Patent No.: US 6,511,638 B2
(45) Date of Patent: Jan. 28, 2003

(54) APPARATUS AND METHOD FOR GENERATING OZONE

(75) Inventor: Teruo Matsuzaki, Chula Vista, CA (US)

(73) Assignee: Robert De La Torre Stone, Vista, CA (US)

( * ) Notice: Subject to any disclaimer, the term of this patent is extended or adjusted under 35 U.S.C. 154(b) by 91 days.

(21) Appl. No.: 09/821,245

(22) Filed: Mar. 29, 2001

(65) Prior Publication Data

US 2002/0139756 A1 Oct. 3, 2002

(51) Int. Cl.$^7$ ................................. B01J 19/08
(52) U.S. Cl. ..................... 422/186.18; 422/186.19
(58) Field of Search ................ 422/186.07, 186.18, 422/186.19

(56) References Cited

U.S. PATENT DOCUMENTS

| | | | |
|---|---|---|---|
| 4,834,948 A | * | 5/1989 | Schmiga et al. ....... 422/186.19 |
| 5,433,927 A | * | 7/1995 | Mausgrover et al. .. 422/186.18 |
| 5,847,494 A | | 12/1998 | Bayliss et al. |
| 6,060,027 A | | 5/2000 | Conrad et al. |
| 6,106,788 A | | 8/2000 | Rau et al. |
| 6,139,809 A | | 10/2000 | Rodden |
| 6,165,423 A | | 12/2000 | Crosbie |
| 6,180,014 B1 | | 1/2001 | Salama |
| 6,190,622 B1 | | 2/2001 | Conrad et al. |
| 6,193,852 B1 | | 2/2001 | Caracciolo et al. |

* cited by examiner

*Primary Examiner*—Kishor Mayekar
(74) *Attorney, Agent, or Firm*—Baker & McKenzie

(57) ABSTRACT

An apparatus and method for generating ozone is provided. An ozone generator comprises a substantially transparent element having ozone-generating means mounted on an inner element area and an outer element area. An enclosure is positioned over the element, and an oxygen-containing gas is directed through the inner element area, creating ozone from a portion of the oxygen-containing gas. The ozone and oxygen-containing gas is then redirected over the outer element area, so that the oxygen-containing gas is at least twice exposed to the ozone-generating means, thereby generating additional ozone.

10 Claims, 3 Drawing Sheets

APPARATUS AND METHOD FOR GENERATING OZONE

FIELD OF THE INVENTION

The present invention generally relates to ozone generation, and more particularly to a method and apparatus for generating ozone for eliminating pollutants from fluids and gasses.

BACKGROUND OF THE INVENTION

Ozone is a powerful oxidant and disinfectant that readily oxidizes organic pollutants, inorganic pollutants, and microorganisms. Ozone is form of oxygen that has three atoms per molecule rather than the two atoms normally found in oxygen. When the extra oxygen atom splits off from the ozone molecule, one of two things happen, disinfection or oxidation. As a disinfectant, these free oxygen atoms quickly destroy bacteria and other microorganisms that they contact. As an oxidant, the free oxygen molecule reacts with existing chemical compounds and yields more benign by-products.

Ozone occurs when an electrical charge molecularly disassociates a stable molecule ($O_2$) and splits it apart leaving two unstable atoms of oxygen. Seeking stability, these atoms attach to other oxygen molecules creating ozone ($O_3$).

Ozone occurs naturally in the atmosphere during lightning strikes and other electric discharge phenomena. Ozone can also be artificially generated by passing air through electric discharge fields. Another method for generating ozone is passing air through ultraviolet (UV) radiation generated by UV lamps. Specifically, ozone can be formed when air or an oxygen-containing gas is exposed to ultraviolet radiation generated in the range from about 100 nanometers to about 260 nanometers.

There are several shortcomings associated with generating ozone through UV lamps. The lifetime of a UV lamp is limited due to the volatile mercury vapor used in the lamp which causes the lamp performance to deteriorate over time. Moreover, the effective ozone generating range from a UV lamp is relatively small, thereby limiting the amount of ozone that can be generated. Finally, these lamps operate at extremely high temperatures which causes the ozone to deteriorate.

Because ozone is formed by the disassociation of oxygen molecules, it is unstable and has a relatively short lifetime. Therefore, to be effective as an oxidizer and disinfectant, the ozone should be immediately inserted into the gas or fluid pollutant stream. In the case of polluted fluids, however, high temperature mercury-vapor UV lamps cannot be placed in the fluid stream because they will burst upon contact with the fluid.

Accordingly, there exists a need for an ozone generator that can generate ozone reliably without deteriorating in performance and can also be placed "in situ" so that the ozone can be inserted into polluted fluids and gases for efficient oxidation and disinfection.

SUMMARY OF THE INVENTION

The present invention alleviates to a great extent the disadvantages of conventional ozone generating devices by providing an apparatus and method for generating ozone without using an ultraviolet mercury vapor lamp. In addition, the present invention exposes an oxygen-containing gas to the ozone generating elements at least twice, thereby increasing ozone generation.

In a preferred embodiment, the ozone generator comprises a substantially transparent tube with an inner mesh electrode arranged around an inner surface of the tube and an outer mesh electrode arranged about an outer surface of the tube. The mesh electrodes communicate with an electrical ground and an electrical power source, thereby forming a multiplicity of ozone-creating arcs that generate ozone. In one embodiment, a substantially transparent jacket encloses the tube and electrodes so that an oxygen-containing gas can be directed down the center of the tube and then redirected around the outside of the tube, thereby exposing the oxygen-containing gas to the ozone-creating arcs at least twice.

In another aspect of the invention, a housing encloses the jacket, the housing including a fluid inlet and fluid exit so that a fluid entering the housing is exposed to the ozone-creating electric arcs through the substantially transparent jacket. In another aspect of the invention, an ozone return line is coupled to the jacket and the housing so that ozone can be introduced into the fluid while the fluid is simultaneously exposed to the ozone-creating electric arcs. In this manner, a polluted fluid can be exposed simultaneously to ozone and to the ozone-creating electric arcs.

Another aspect of the present invention comprises a floatable ozone generator. The floatable ozone generator is structured to float on a fluid surface so that the volatile ozone can be produced "in situ" and immediately introduced into the fluid, thereby maximizing the efficiency of the ozone generator. A floatable ozone generator would comprise a floatable housing containing a jacket which contains a substantially transparent tube with the tube containing an inner mesh electrode and outer mesh electrode. The inner and outer mesh electrodes communicate with an electrical ground and an electrical power source forming a multiplicity of ozone-creating electric arcs. Air or another oxygen-containing gas is introduced into the housing and thus into the jacket. As the oxygen-containing gas progresses down the jacket, it passes through and over the electrodes located on the tube thereby creating ozone. The ozone is then directed outside of the housing and into the fluid for disinfection and/or oxidation of pollutants present in the fluid.

These and other features and advantages of the present invention will be appreciated from review of the following detailed description of the invention, along with the accompanying figures in which like reference numerals refer to like parts throughout.

BRIEF DESCRIPTION OF THE DRAWINGS

The nature, goals, and advantages of the invention will become more apparent to those skilled in the art after considering the following detailed description when read in connection with the accompanying drawing in which like reference numerals identify like elements throughout wherein.

It will be recognized that some or all of the Figures are schematic representations for purposes of illustration and do not necessarily depict the actual relative sizes or locations of the elements shown.

DETAILED DESCRIPTION OF THE INVENTION

In the following paragraphs, the present invention will be described in detail by way of example with reference to the attached drawings. Throughout this description, the preferred embodiment and examples shown should be considered as exemplars, rather than as limitations on the present invention. As used herein, "the present invention" refers to any one of the embodiments of the invention described herein.

Existing apparatus and methods for generating ozone have several shortcomings. Specifically, mercury-vapor ultraviolet (UV) lamps operate at relatively high temperatures and have short lifetimes due to the volatile nature of the mercury vapor. For the disinfection and/or oxidation of polluted fluids, the UV lamps must be placed away from the fluid stream because fluid contacting the UV lamp will cause the lamp to burst. However, because ozone is an unstable molecule, it must be placed close to the fluid or gas to be treated to be effective. Systems that transport the ozone over a distance are inefficient because a large percent of the ozone stabilizes into oxygen. The challenge is to construct a device for generating ozone that will not deteriorate in performance over time, and can be placed close to, or within the fluid or gas to be disinfected.

The present invention provides ozone generation through generating a multiplicity of electric arcs that radiate ultraviolet radiation in an ideal frequency of about 189 nanometers. The ultraviolet radiation converts oxygen into ozone which is then delivered immediately to the gas or fluid to be disinfected and/or oxidized. In one aspect of the present invention, an oxygen-containing gas is exposed to the ozone-creating ultraviolet radiation at least twice, thereby maximizing the generation of ozone. In another aspect of the present invention, a fluid to be disinfected is simultaneously exposed to ozone gas and ultraviolet radiation which creates more ozone from oxygen present in the fluid. This simultaneous "double exposure" of ozone and ultraviolet radiation rapidly disinfects and oxidizes the pollutants present in the fluid.

Figure 1:
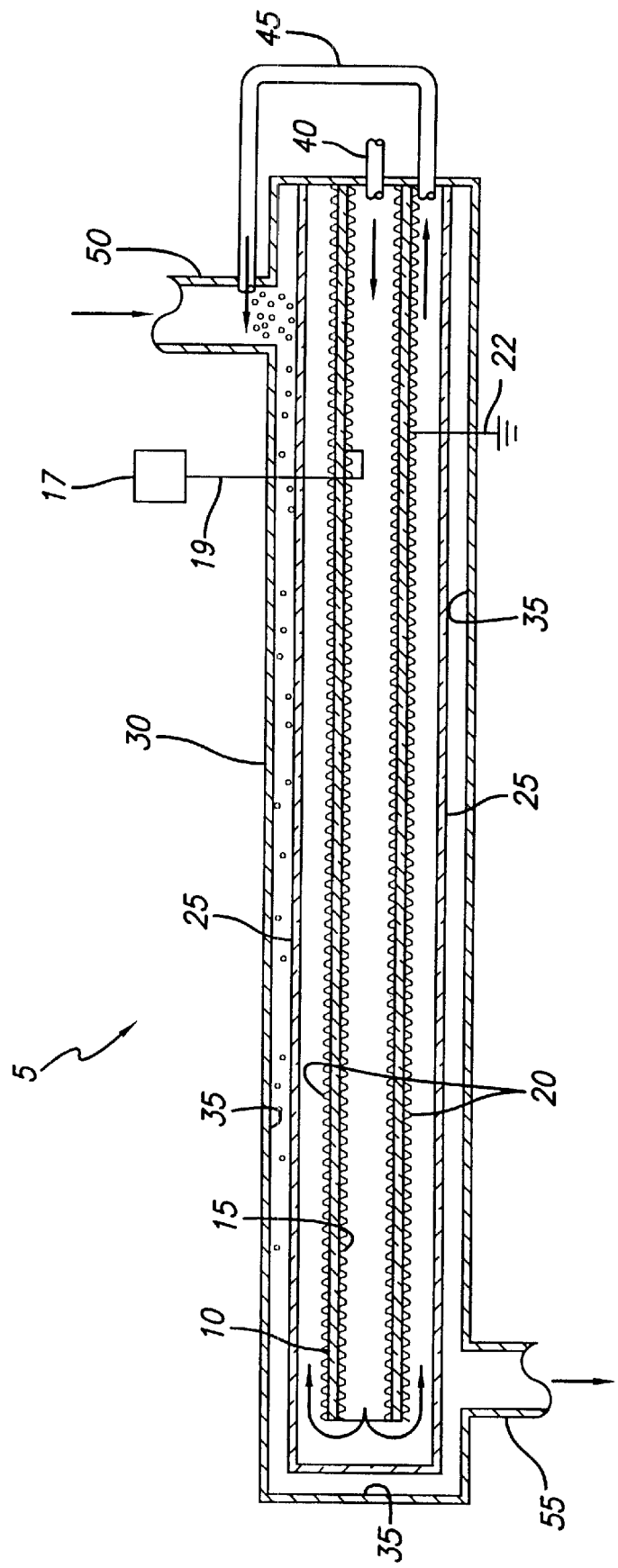
FIG. 1 is a cross-section view of an ozone generator constructed according to the present invention.

Referring to FIG. 1, an apparatus for generating ozone 5 is illustrated. An interior element or tube 10 is located within a jacket 25. The tube 10 is hollow with two open ends. Positioned around an interior of the tube 10 is an inner mesh 15 and positioned around an outer surface of the tube 10 is an outer mesh 20. Two possible types of mesh include number 10 mesh and number 14 mesh which have 10 squares and 14 squares per inch, respectively. A preferred embodiment mesh is a number 10 mesh made of stainless steel, which is about 0.30 inches in diameter. Preferably the stainless steel is 316 stainless steel but 304, 316L and 405 stainless steel and titanium can also be employed. Other types of conductive wires can be employed and need not be in the form of a mesh. For example, one or more wires wound about an inner surface and outer surface of the tube 10 could also be employed. Because of the oxidative nature of ozone, the material used for the mesh or wires ideally is resistant to oxidation.

An electrical energy source 17 supplies energy through connector 19 to the inner mesh 15. The outer mesh 20 is connected to an electrical ground through connector 22. It will be appreciated that the power and ground connections can be reversed. In operation, the electrical energy source 17 provides a voltage to the inner mesh 15. When the amount of voltage is sufficient, an arc is formed that passes through the tube 10 to the outer mesh 20. The amount of voltage necessary to create an arc can vary depending upon the type of material and thickness used in the tube 10. In one embodiment, about 10,000 volts are required when a 1 mm. quartz tube 10 is employed; about 20,000 volts are required when a 2 mm. quartz tube 10 is employed; and about 25,000 volts are required when a 2.5 mm. thick quartz tube 10 is employed. Preferably, the electrical energy source 17 is obtained from Plasma Technics, Inc. of Racine, Wis.

As defined herein, a tube includes any type of pipe, cylinder or other essentially elongated hollow object having a circular or non-circular cross-section. In a preferred embodiment, the tube 10 is a circular tube having an outer diameter of about 1.5 inches. Other diameters can also be employed depending upon the desired amount of ozone to be generated.

Preferably, the tube 10 is manufactured from quartz. This type of tube is commercially available and is referred to as a fused quartz, fused silica, vitreous silica, or synthetic fused silica tube. Fused quartz made from synthetic fused silica is highly resistant to discoloration from prolonged exposure to ultraviolet radiation. Hence, tube 10 preferably is manufactured from synthetic fused silica. Moreover, a tube 10 constructed from synthetic fused silica transmits ultraviolet radiation wavelengths from about 160 nanometers to over 250 nanometers. The present invention creates ultraviolet radiation in an ideal ozone-generating wavelength of about 185 nanometers. Other ultraviolet wavelength frequencies, ranging from about 150 nanometers to about 270 nanometers, can also be generated by the present invention to suit ozone generating requirements for specific applications. A preferred embodiment tube 10 is a type 214 GE quartz tube manufactured by the General Electric Corporation of Cleveland, Ohio. Other types of GE tubing that can be employed include 221, 214LD, 224, and 244. These quartz tubes constructed of synthetic fused silica have a high UV transmittance and a high level of resistance to solarization. In addition, these tubes have a low coefficient of thermal expansion and an unusually high thermal shock resistance. For example, tube 10 can be heated to extremely high temperatures and then cooled quickly without cracking. This characteristic is important in some embodiments of the present invention described below. Moreover, synthetic fused silica employed to manufacture tube 10 of the present invention can withstand temperatures up to about 1600 degrees centigrade. This allows the tube 10 to absorb the heat generated by the arcs passing through the tube 10 during extended periods of operation.

Referring again to FIG. 1, surrounding the tube 10 and the inner and outer meshes 15 and 20 positioned about the tube 10, is jacket 25. In the embodiment illustrated in FIG. 1, the jacket 25 is substantially transparent and constructed of the same quartz or silica used to construct the tube 10. The jacket 25 therefore has the same thermal, optical and other qualities as the tube 10. Illustrated in FIG. 1, the jacket 25 is constructed to direct the flow of oxygen-containing gas over the outer mesh 20. For example, an inlet 40 is located at an end of the tube 10 and oxygen-containing gas is directed through the inlet and along the interior of the tube 10. The oxygen-containing gas is exposed to the inner mesh 15 that is generating a multiplicity of electric arcs, which radiate UV radiation. The oxygen in the oxygen-containing gas is converted to ozone upon exposure to the UV radiation as the gas progresses along the length of tube 10. Upon reaching the end of tube 10, the oxygen-containing gas contacts the inner surface of the jacket 25 and is redirected along the outer surface of the tube 10 contacting the outer mesh 20 and again being exposed to the ultraviolet radiation generated by the electric arcs present in the outer mesh 20. This second exposure to the ultraviolet radiation generates even more ozone, significantly increasing the amount of ozone that is generated and increasing the efficiency of the ozone generator 5.

In one embodiment, the diameter of the jacket 25 is about one-half inch greater than the diameter of the tube 10, but other relative diameter relationships are possible. Moreover, as discussed above, the tube 10 and jacket 25 need not have circular cross-sections. After the oxygen-containing gas is exposed to both the inner mesh 15 and the outer mesh 20, it passes through ozone return line 45 positioned at one end of jacket 25.

Again referring to FIG. 1, housing 30 encompasses both the tube 10 and the jacket 25 and is structured to contain a fluid and direct the fluid around the jacket 25. Housing 30 includes a fluid inlet 50 and a fluid exit 55. Other arrangements for passing fluids over the jacket 25 are contemplated, such as two substantially parallel plates having two open ends that permit the passage of the fluid from one end of the plate to the other with the jackets 25 positioned perpendicular to the flow of fluid. Alternatively, several fluid inlets 50 and fluid exits 55 may be positioned along the housing 30. In the embodiment illustrated in FIG. 1, a single fluid inlet 50 includes a ozone return line 45. The ozone return line 45 delivers ozone from the jacket 25 to the fluid inlet 50. As a fluid enters the fluid inlet 50, ozone is injected into the fluid. Because the jacket 25 is substantially transparent to ultraviolet radiation generated by the electric arcs formed between the inner mesh 15 and the outer mesh 20, additional ozone is formed in the fluid from oxygen present in the fluid. Therefore, the present invention simultaneously injects a fluid with ozone gas and exposes the fluid to ultraviolet radiation which creates additional ozone in the fluid. In this manner, the present invention is highly effective in generating ozone for disinfecting and/or oxidizing pollutants in fluids. The fluid then passes through the housing 30 and exits from fluid exit 55.

An alternative embodiment of the invention illustrated in FIG. 1 can include a reflective surface 35 on the interior surface of the housing 30. A reflective surface 35 reflects the ultraviolet radiation generated by the inner mesh 15 and outer mesh 20, thereby exposing the fluid to additional ultraviolet radiation. The reflective surface 35 can be constructed in several ways, preferably the housing 30 has a polished interior surface, but alternatively stainless steel, aluminum, copper, silver, gold or other reflective materials may be deposited on the housing 30. Other types of methods for applying a reflective surface to housing 30 are also contemplated, including applying films or constructing the housing 30 of stainless steel, aluminum, copper or other reflective materials.

Figure 2:
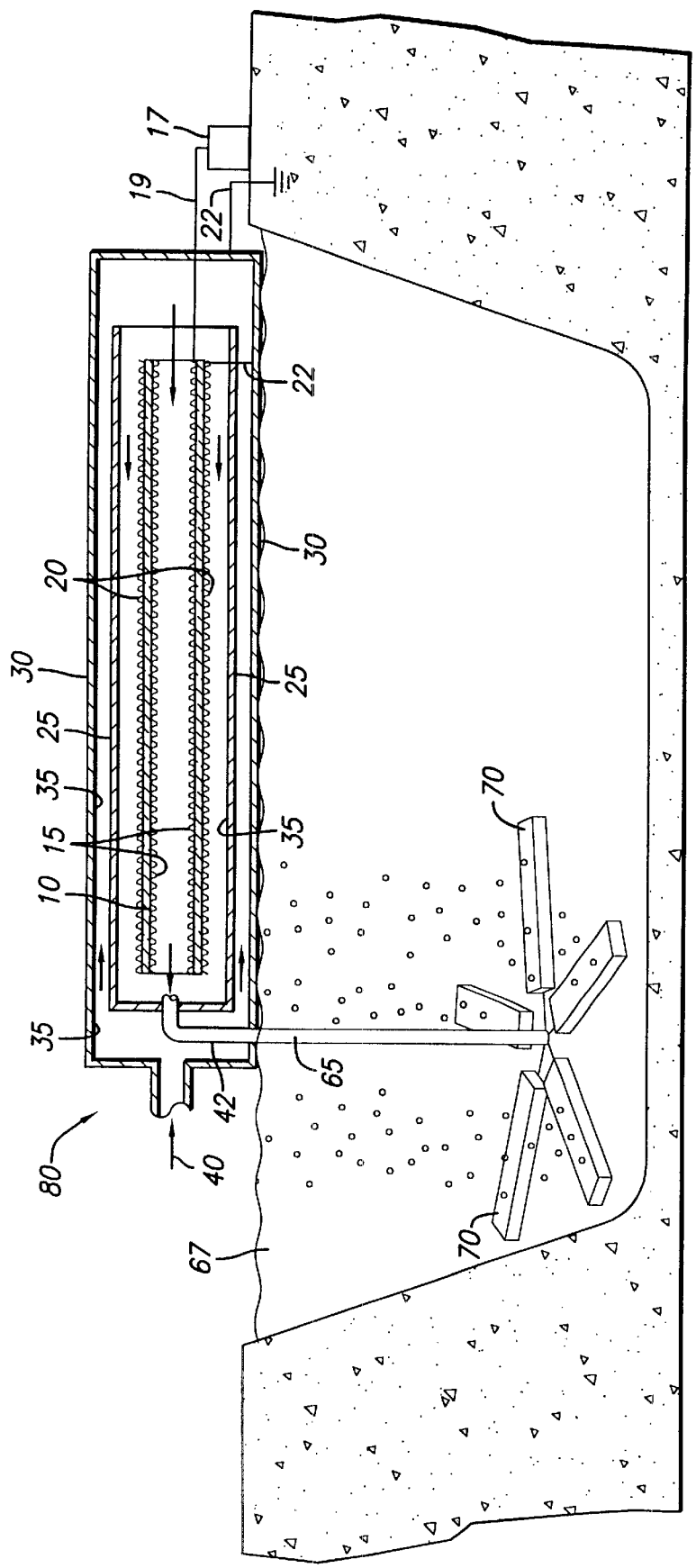
FIG. 2 is a cross-section view of an alternative embodiment ozone generator constructed according to the present invention.

Referring to FIG. 2, an alternative embodiment of the present invention is illustrated. Floating ozone generator 80 is structured to float on a fluid surface, such as water, so that ozone can be generated "in situ." Floatable ozone generator 80 includes a tube 10 similar to that contained in ozone generator 5 with inner mesh 15 and outer mesh 20 positioned around the interior and exterior of tube 10. Tube 10, inner mesh 15 and outer mesh 20 have the same or similar characteristics as found in the ozone generator 5. In this embodiment, the tube 10 is positioned in a jacket 25 that has an open end and a substantially closed end containing an ozone or air exit 42. In a similar manner to that described above, the inner mesh 15 and outer mesh 20 are respectively connected to an electrical energy source 17 and an electrical ground 22. A voltage is applied to the inner mesh 15 that creates a multiplicity of electric arcs, between and among the inner and outer meshes 15 and 20, respectively, which generate ultraviolet radiation that creates ozone in an oxygen-containing gas introduced through and around the tube 10. The oxygen-containing gas is introduced through air inlet 40 located in housing 30, which is structured to float on a fluid surface.

In the embodiment illustrated in FIG. 2, the jacket 25 may include a reflective surface 35 on the inner surface of the jacket 25. As discussed above, the reflective surface 35 will reflect ultraviolet radiation generated by the electric arcs, thereby increasing the amount of ozone generated as the oxygen-containing gas progresses from the entry of the jacket 25 to the exit 42. The types of reflective surfaces 35 that can be employed in the floating ozone generator 80 discussed above, in connection with ozone generator 5.

One or more aerators 70 are connected to the air exit 42 by a tube 65. The aerators are structured to distribute the ozone delivered from the floating ozone generator 80 into small bubbles, that are introduced into the fluid 67, thereby disinfecting and oxidizing any pollutants present in the fluid 67. In a preferred embodiment, the aerators are constructed of pumice stone that is structured to generate small bubbles. One advantage of the present invention is that tube 65 not only transports ozone generated by the floating ozone generator 80, but also acts as a heat transfer element because the fluid 67 cools the tube 65 thereby transferring heat from the ozone to the fluid 67, cooling and thereby stabilizing the ozone. Moreover, the housing 30 also contacts the fluid 67 and also acts as a heat transfer element.

In one embodiment, the floating ozone generator 80 is employed in a shrimp farm or other type of aquaculture environment, such as a trout, shellfish, or salmon farm. The floating ozone generator 80 is placed in a shrimp pond to supply ozone through the aerators 70 for disinfecting and oxidizing pollutants present in the shrimp pond. Air is pumped through air inlet 40 at approximately 20 pounds per square inch so that ozone routed through the air exit 42 can reach the aerators 70 located approximately ten feet below the fluid surface 67. Other air pressures can also be employed, depending upon the depth of the pond. For example, other aquaculture systems may use deeper pools that require a higher air pressure so that the ozone can be pumped to the bottom of the pool.

Figure 3:
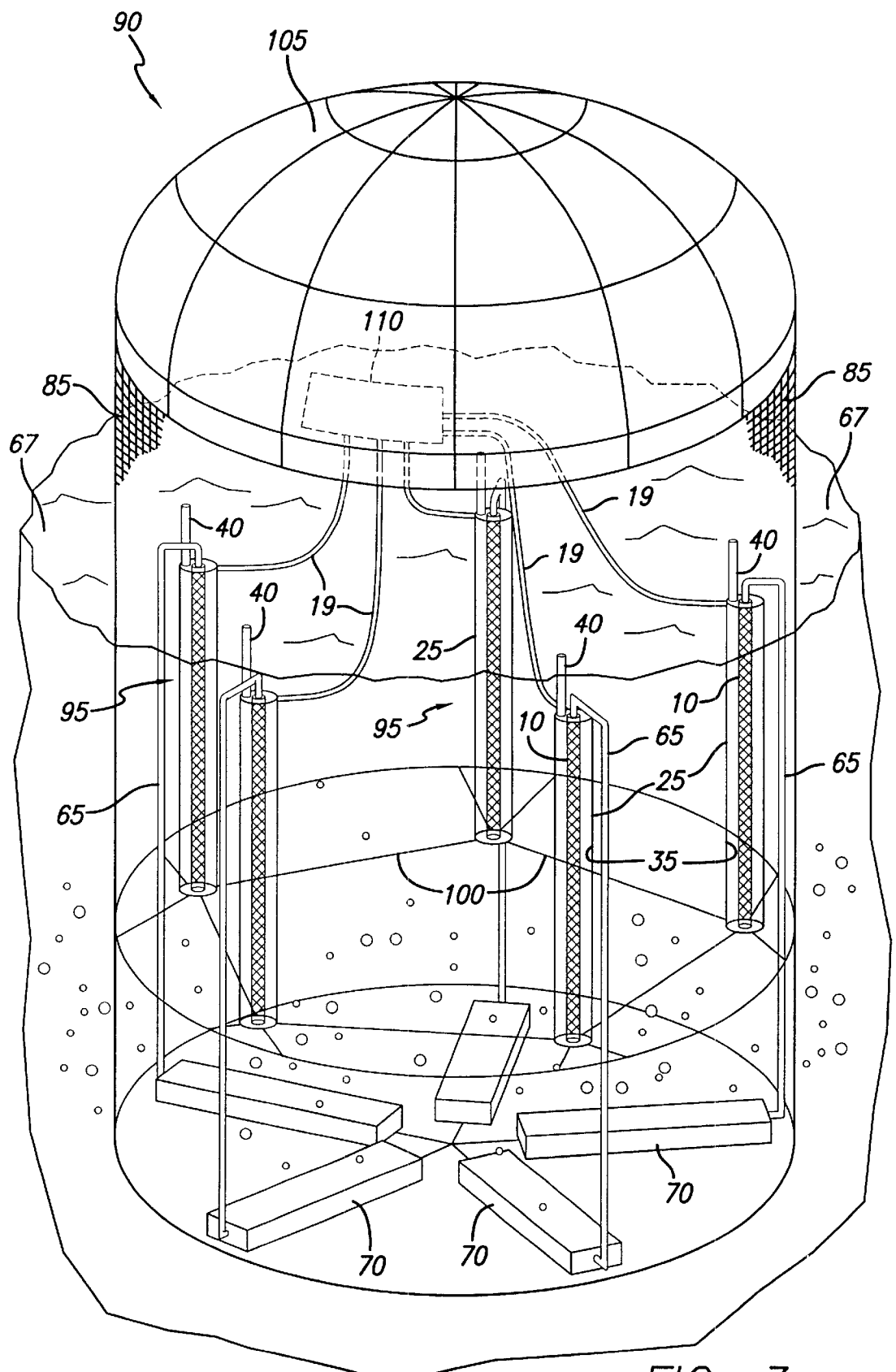
FIG. 3 is yet another embodiment of an ozone generator constructed according to the present invention.

Referring to FIG. 3, a multi-element ozone generator 90 is illustrated. This embodiment of the present invention is structured to operate substantially submerged in a large body of water 67 such as bays, rivers, reservoirs or other bodies of water 67 that are polluted. A water-permeable housing 85 encloses a plurality of ozone generating units 95. The number of ozone generating units 95 is limited only by the size of the water-permeable housing 85. Preferably, the water-permeable housing 85 is in the form of a screen, grill, lattice or other arrangement structured to permit the passage of water. Mounted within the water-permeable housing 85 are one or more ozone generating units 95 that incorporate many of the features of the ozone generator 5 illustrated in FIG. 1. Specifically, a tube 10 includes an inner mesh 15 wrapped around an interior surface of the tube and an outer mesh 20 wrapped about an outer surface of the tube 10. The tube 10 is positioned in a jacket 25, the jacket 25 and the tube 10 both constructed of a substantially transparent quartz. The jacket 25 is positioned within the multi-element ozone generator 90 by tethers 100. The tethers 100 can be rigid or they can allow relative movement of the ozone generating units 95 relative to the water-permeable housing 85. As discussed above with reference to the ozone generator 5, the inner mesh 15 and outer mesh 20 are connected to an electrical energy source 17 (not illustrated) and an electrical ground 22 (not illustrated). In this embodiment, the electrical energy source 17 may comprise a plurality of photovoltaic cells 105 mounted on top of the water-permeable housing 85. Photovoltaic cells convert solar energy into a direct current that is changed to alternating current by converter 110 that then supplies electrical energy to each inner mesh 15 in each ozone generating unit 95. Alternatively, the multi-element ozone generator 90 can be supplied with electrical energy through a power source described above in connection with the ozone generator 5.

Each of the ozone generating units 95 includes an air inlet 40 that receives air from a pressurized source (not shown). In a fashion similar to that described in connection with the ozone generator 5, an oxygen-containing gas is injected into the interior of the tube 10 where it contacts the inner mesh 15 and is exposed to the ultraviolet radiation generated by the electric arcs that are formed between the inner mesh 15 and the outer mesh 20. When the air has progressed the entire length of the tube 10, it then contacts the jacket 25 which redirects the air along the outer mesh 20 where it is again exposed to the ultraviolet radiation generated by the electric arcs. The generated ozone is then pumped from jacket 25 through tube 65 to aerator 70. The aerators 70 are located at the bottom of the water-permeable housing 85 and may be supported by a fluid-permeable screen, grill or lattice. Alternatively, the water-permeable housing 85 may not include a lower surface and the aerators 70 may be structured to float in the fluid and may be tethered together or float freely in the fluid 67.

As discussed above in connection with the floating ozone generator 80, the aerators 70 are constructed of pumice stone or other suitable material for generating small bubbles of ozone. The ozone is released through the aerator 70, which progresses toward the surface of the fluid 67 disinfecting and oxidizing any pollutants present in the fluid. In addition, in one embodiment of the multi-element ozone generator 90, the jackets 25 are substantially transparent to ultraviolet radiation generated by the inner mesh 15 and outer mesh 20 and therefore the jacket 25 allows the passage of ultraviolet radiation through the jacket 25. Ultraviolet radiation contacting the water 67 converts oxygen it contacts into ozone, creating additional ozone in the water 67. In another embodiment of the multi-element ozone generator 90, the jacket 25 contains a reflective surface 35 that reflects the ultraviolet radiation into the interior of the jacket 25 thereby increasing the exposure of ultraviolet radiation to the air that is injected into the air inlet 40.

Thus, it is seen that an apparatus and method for generating ozone is provided. One skilled in the art will appreciate that the present invention can be practiced by other than the preferred embodiments, which are presented in this description for purposes of illustration and not of limitation, and the present invention is limited only by the claims that follow. It is noted that various equivalents for the particular embodiments discussed in this description may practice the invention as well.

What is claimed is:

1. An ozone generator comprising:

a substantially transparent tube including two ends, with one end including an inlet for oxygen-containing gas;

an inner mesh electrode arranged about an inner surface of the tube;

an outer mesh electrode arranged about an outer surface of the tube, the outer and inner mesh electrodes selectively connected to an electrical ground and an electrical power source, thereby forming a multiplicity of ozone-creating electric arcs that generate ozone in the oxygen-containing gas;

a substantially transparent jacket structured to enclose the tube and electrodes, the jacket including a gas exit;

a housing structured to enclose the jacket, the housing including a fluid inlet and a fluid exit; and an ozone return line coupled to the gas exit and the housing, so that a fluid passing through the housing is simultaneously exposed to ozone and an ultraviolet radiation produced by the ozone-creating electric arcs.

2. The ozone generator of claim 1, wherein an inner surface of the housing is structured to reflect a radiation generated by the electric arcs.

3. The ozone generator of claim 1, further comprising a reflective surface located on an inner surface of the housing, the reflective surface selected from the group consisting of: a polished inner surface of the housing, stainless steel, aluminum, copper, silver, gold and films of any one of stainless steel, aluminum, copper, silver and gold.

4. The ozone generator of claim 1, wherein the multiplicity of ozone-creating electric arcs radiate wavelengths between about 150 nanometers to about 270 nanometers.

5. The ozone generator of claim 1, wherein at least one of the tube and the jacket are comprised of a material selected from the group consisting of: fused silica, fused quartz, synthetic fused silica, and vitreous silica.

6. The ozone generator of claim 1, wherein at least one of the tube and the jacket transmit wavelengths between about 160 nanometers to about 300 nanometers.

7. The ozone generator of claim 1, wherein at least one of the inner and outer mesh electrodes is selected from the group consisting of: 304 stainless steel, 316 stainless steel, 316L stainless steel, 405 stainless steel and titanium.

8. The ozone generator of claim 1, wherein at least one of the inner and outer mesh electrodes is selected from the group consisting of: number 10 mesh and number 14 mesh.

9. The ozone generator of claim 1, wherein the electrical power source is selected from the group of power sources consisting of devices with a voltage output that can range from 6 kilovolts to over 25 kilovolts, with an output frequency that can range from 50 hertz to over 2,000 hertz, and a power level that can range from 1 kilowatt to 4 kilowatts.

10. The ozone generator of claim 1, wherein the ozone return line is coupled to the fluid inlet.

* * * * *